United States Patent [19]

Petrofsky

[11] Patent Number: 4,785,813

[45] Date of Patent: Nov. 22, 1988

[54] APPARATUS FOR ASSISTING MUSCULAR CONTRACTION

[75] Inventor: Jerrold S. Petrofsky, Beavercreek, Ohio

[73] Assignee: Wright State University, Dayton, Ohio

[21] Appl. No.: 829,890

[22] Filed: Feb. 18, 1986

[51] Int. Cl.[4] ............................ A61N 1/00; H05G 1/00
[52] U.S. Cl. ..................................... 128/421; 128/733
[58] Field of Search ............... 128/422, 421, 423, 741, 128/721, 733, 731, 419 R

[56] References Cited

U.S. PATENT DOCUMENTS

4,431,000  2/1984  Butler .................................. 128/421
4,582,049  4/1986  Ylvisakev ........................... 128/421

*Primary Examiner*—Francis J. Jaworski
*Assistant Examiner*—George Manuel
*Attorney, Agent, or Firm*—Biebel, French & Nauman

[57] ABSTRACT

A system for assisting contraction of a partially paralyzed muscle. The system uses a pair of electrode terminals which sense voluntary EMG signals at the site of the muscle and periodically transmit appropriately corresponding higher level stimulation signals. Stimulation signals are generated by a pulsed stimulator operating under control of an amplifier arrangement connected to receive the EMG signals from the electrode terminals. A transistor switch interrupts the amplifier output in synchronism with the generation of stimulation signals. A pair of back-to-back diodes are positioned between the electrode terminals for limiting the signals which are applied to the amplifier.

13 Claims, 6 Drawing Sheets

APPARATUS FOR ASSISTING MUSCULAR CONTRACTION

BACKGROUND OF THE INVENTION

This invention relates to the field of assisting persons afflicted with partial paralysis. Such partial paralysis may be the result of a stroke or mild spinal cord injury. In either event, such persons customarily are able to move their limbs but only ineffectively and at reduced contraction levels.

In recent years there has been a great deal of activity directed toward restoring useful movement to totally paralyzed limbs. Such effort has produced computer controlled stimulation systems for producing leg exercise as disclosed in Petrofsky et al. U.S. Pat. No. 4,480,830 and in Petrofsky et al. U.S. Pat. No. 4,499,900. Computer controlled arm movement has also been developed as disclosed in Petrofsky U.S. Pat. No. 4,558,704.

During muscular contraction by non-handicapped persons the brain generates electromyographic signals which are transmitted by the spinal cord to motor control points for the muscles which are to contract. In many cases of total paralysis there is a break in the communication link between the brain and the motor control point, but the muscle itself is otherwise undamaged. In such cases it has been found possible to generate stimulation signals which are artificial substitutes for the natural electromyographic signals. The stimulation signals are applied to the muscles through transcutaneous electrodes. It is also possible to achieve muscle stimulation through surgically buried electrodes.

In the case of partial paralysis there is no need to create an artificial substitute for the natural electromyographic signals. The signals are not interrupted but are merely degraded. It is therefore desirable to utilize such electromyographic signals for controlling functional electrical stimulation.

Prior art devices have used electromyographic signals in a variety of applications. For example, apparatus as disclosed in Tanie et al. U.S. Pat. No. 4,314,379 senses electromyographic signals for controlling a servo device connected to operate an artificial arm. A system has also been proposed for measuring electromyographic signals on a paralyzed person's upper body and using those signals for controlling stimulation of the lower extremities. See Graupe et al. "Electromyographic Control of Functional Electrical Stimulation in Selected Patients", *Orthopedics*, July 1984, pp. 1134–1138. Both of these prior art approaches sense electromyographic signals at one location and control activity at a different location.

Another system as disclosed in Vincent et al. U.S. Pat. No. 3,628,538 measures electromyographic signals at a motor control point and uses the measurement for control of stimulation signals applied at the same point. The system is used for stimulating bladder control muscles. Accordingly, it utilizes electrical circuitry which listens to electromyographic signals for a period of about 50 milliseconds and then stimulates the bladder control muscles for a period of about 10 seconds. Such a system is not suitable for smooth continuous control of arm or leg activity.

SUMMARY OF THE INVENTION

Muscular contraction is assisted in accordance with the present invention by electrodes located at the site of the muscle to be assisted. These electrodes receive voluntary electromyographic (EMG) signals and transmit them to an amplifier. The amplifier then amplifies the EMG signals to produce a correspondingly higher amplitude control signal. The control signal then is transmitted to a stimulator which generates a series of stimulation pulses each having a stimulation effectivity which depends variably upon changes in the level of the control signal. These stimulation pulses are supplied to the electrodes.

Signal limiting means are provided at the input side of the amplifier in order to avoid amplification of signals significantly in excess of expected EMG signals. This avoids saturation of the amplifier by high amplitude stimulation pulses. Switch means are also provided for disconnecting the stimulator from the amplifier while stimulation pulses are being delivered to the electrodes. This assures that stimulation pulses are generated only in response to EMG signals. Thus uncontrolled feedback of the stimulation signals is avoided.

In a typical embodiment the electrodes comprise a pair of terminals across which stimulation pulses are delivered at a potential difference of about 50 volts. The stimulation pulses may have a duration of about 300 microseconds and be repeated at 15 millisecond intervals. Preferably the switch means disconnects the stimulator input during the stimulation pulse period and thereafter during a pause period which extends for a time approximately two-thirds of the time between stimulation signals.

Accordingly it is an object of the present invention to assist muscular contraction by amplifying weak electromyographic signals and using the amplified signals for control of stimulation signals which are applied to the assisted muscle.

Other objects and advantages of the invention will be apparent from the following description, the accompanying drawings and the appended claims.

DESCRIPTION OF THE PREFERRED EMBODIMENT

Figure 1:
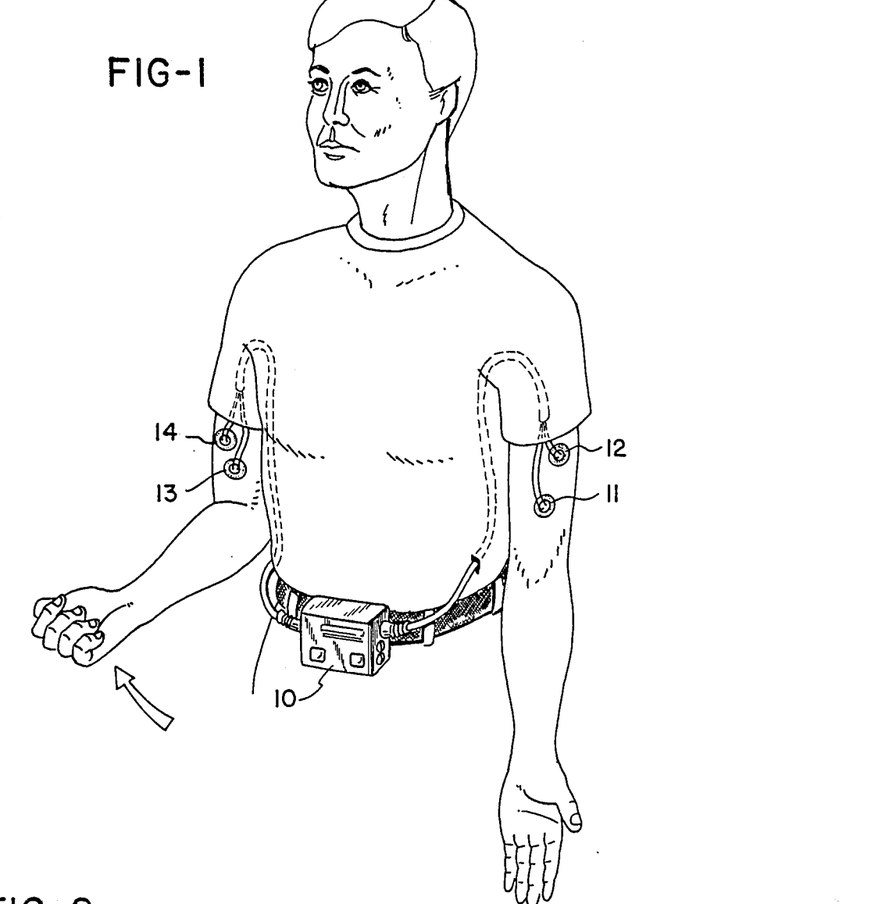
FIG. 1 illustrates the apparatus of the present invention as applied to the biceps muscles of a human subject.
Figure 2:
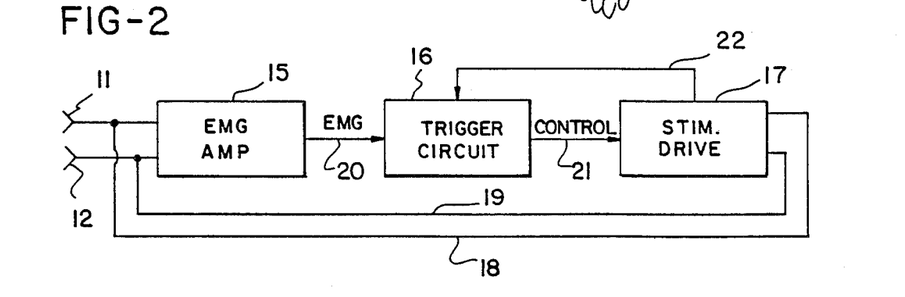
FIG. 2 is a generalized block diagram of the circuitry of the present invention.

In a typical application the present invention may be packaged in a case 10 for attachment to the clothing of a subject person, as illustrated in FIG. 1. Packaged within case 10 are an EMG amplifier 15, a trigger circuit 16 and a stimulation drive circuit 17 operatively interconnected, as generally illustrated in FIG. 2. The system also includes a pair of electrodes 11, 12 which may be configured as transcutaneous electrodes for application to the skin of the subject person in a region above a muscle to be assisted. As illustrated in FIG. 1, electrodes 11, 12 may be positioned above the biceps muscles of the left arm. A similar pair of electrodes 13, 14 may be secured to the skin of the subject person above the right biceps muscles. It will be understood that electrodes 13, 14 have their own associated EMG amplifier, trigger circuit and stimulation driving circuit as illustrated in FIG. 2. It will also be understood that the illustration of the invention for assisting contraction of the biceps muscles is merely exemplary. The invention readily may be used for assisting contraction of other muscles of the body.

EMG amplifier 15 is connected for receiving and amplifying EMG signals present at electrodes 11, 12. The amplified EMG signal is applied via line 20 through trigger circuit 16 for further amplification and the gating. A resulting control signal is applied via line 21 to stimulation driving circuit 17. That circuit has outputs which appear on lines 18, 19 and 22. The output on lines 18 and 19 is a pulsed stimulation signal which is current controlled in correspondence with variations in the amplitude of the control signal appearing on line 21. The stimulation signal on lines 18, 19 is applied to electrodes 11, 12 for stimulation of a muscle lying therebeneath.

Stimulation driving circuit 17 generates stimulation signals on lines 18, 19 in a pulsed format under synchronizing control of a synchronizing produced by timer means, as hereinafter described in detail. That same synchronizing signal is via line 22 to trigger circuit 16. Trigger circuit 16 uses the synchronizing signal for switching off the control signal on line 21 during generation of pulses on lines 18, 19 and for a short period of time thereafter, as illustrated by the timing diagram of FIG. 6. Preferably the stimulation pulses have a duration of about 300 microseconds, and this is followed by a pause period of about 10 milliseconds. Thereafter the EMG signals are sensed for about 5 milliseconds, and the cycle is repeated.

Figure 3:
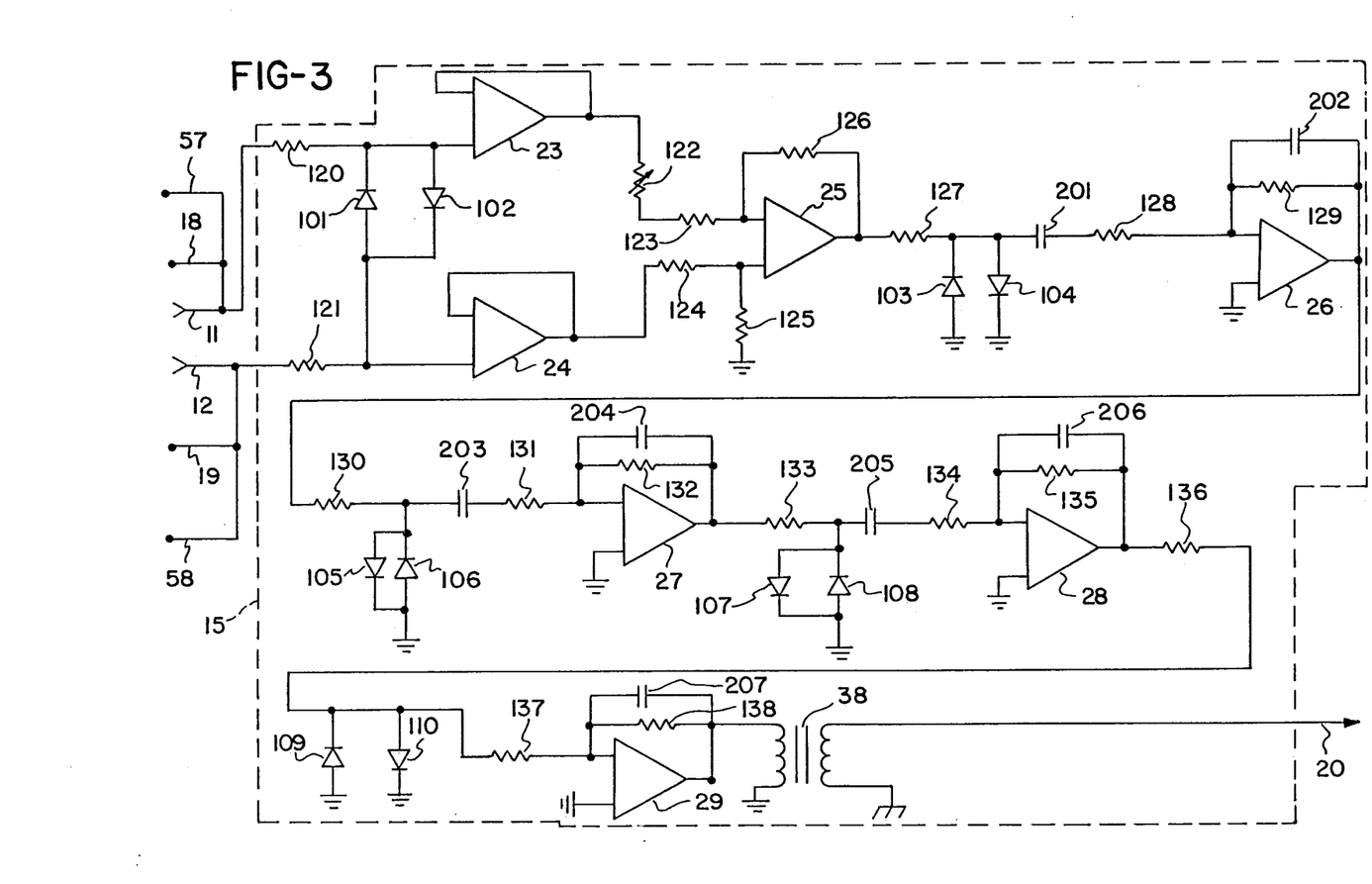
FIG. 3 is an electrical schematic diagram of an EMG sensor.

Referring now to FIG. 3, EMG amplifier 15 will be seen to comprise a series of amplifier stages, each of which has an associated upstream pair of parallel back-to-back diodes. The first such diode pair are diodes 101, 102 which are interposed between electrodes 11, 12 and a pair of operational amplifiers 23, 24 connected for operation as voltage followers. Diodes 101, 102 function as signal limiters. For signals having an amplitude of less than about 300 microvolts, diodes 101, 102 are non-conductive, so that amplifiers 23, 24 follow such signals faithfully. When signals in excess of about 300 microvolts are applied across electrodes 11, 12 then diodes 101, 102 become conductive and the signals received by electrodes 11, 12 are shunted past amplifiers 23, 24.

Typically a partially paralyzed person may generate electromyographic signals in an A.C. format at an RMS level of about 100 microvolts for sensing by electrodes 11, 12. Such signals are readily sensed and followed by amplifiers 23, 24. However, stimulation signals applied via lines 18, 19 to electrodes 11, 12 may have a potential difference of about 50 volts, which is greatly in excess of the conduction threshold of diodes 101, 102. Such signals therefore are not applied to amplifiers 23, 24, and saturation thereof is avoided. Such saturation, if not avoided, would persist for a period of time longer than the OFF period provided by trigger circuit 16.

As also illustrated in FIG. 3, there is a variable resistor 122 at the output side of amplifier 23 for balancing the impedance and thereby increasing the common mode rejection ratio at the input terminals of the next amplifier stage. The resistance of resistor 122 is set forth in Table I. Table I also sets forth identifying information for other components illustrated in FIGS. 3-5.

The output signals from amplifiers 23, 24 are applied to differential amplifier 25 for amplification by a factor of about 3. The amplified output signal from differential amplifier 25 is then additionally amplified by a second stage amplifier 26 which has an associated pair of signal limiting diodes 103, 104 It will be appreciated that noise generated by the stimulation signals and having an amplitude up to the conduction threshold of diodes 101, 102 is passed by voltage followers 23, 24 and amplified by differential amplifier 25. That noise is short circuited to around by diodes 103, 104. These diodes have no effect, however, upon electromyographic signals which are amplified by differential amplifier 25 and which are still well below the conduction threshold of the diodes. These signals pass through coupling capacitor 201 for application to amplifier 26. Amplifier 26 provides further amplification for the EMG signals by a factor of 10. An associated feedback capacitor 202 provides low pass filtering and causes rejection of high frequency noise.

As illustrated in FIG. 3, EMG sensor 15 has three additional amplifier stages associated with amplifiers 27, 28 and 29. Diodes 105 through 110 provide signal limiting for each of these stages in like manner as the signal limiting provided by diodes 103, 104 for amplifier 26. The five illustrated amplifier stages provide a combined amplification factor of about 3000. This boosts the received EMG signals up to a level of about 300 micro volts for application to the primary coil of transformer 38. This transformer is an isolation transformer and provides no amplification.

Figure 4:
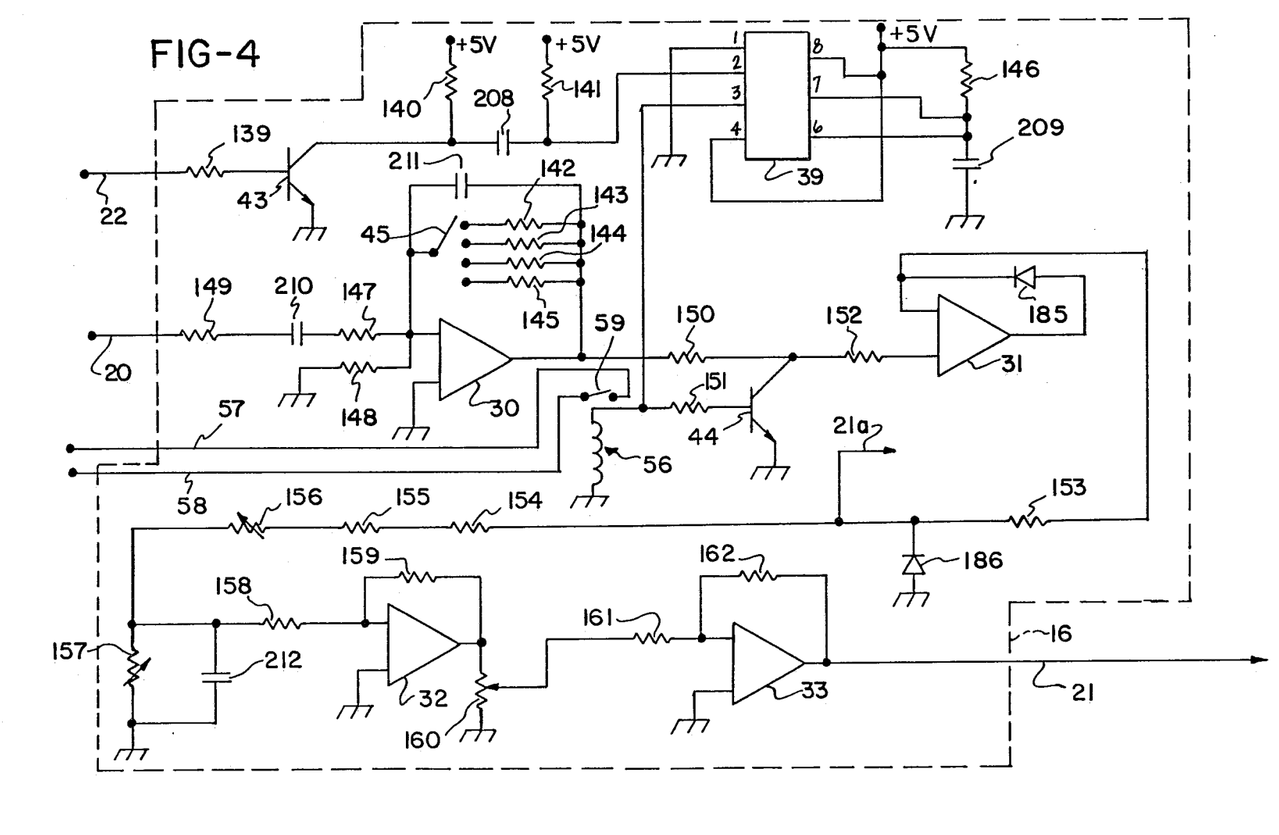
FIG. 4 is an electrical schematic diagram of a trigger circuit.

Amplified EMG signals are applied via line 20 to another amplifier 30 in trigger circuit 16 (FIG. 4). That amplifier has four associated feedback resistors 142-145 which may be individually selected by a switch 45. Switch 45 provides manual control of gain for different degrees of paralysis. By positioning switch 45 the amplification of amplifier 30 may be adjusted from about 10 to 1000.

Output signals from amplifier 30 are applied to the input side of amplifier 31 and also to the collector terminal of NPN transistor 44. The base terminal of transistor 44 is connected to the output terminal of integrated circuit 39, so that transistor 44 functions as a switch. When terminal No. 3 of integrated circuit 39 goes HI, transistor 44 is rendered conductive and output signals from amplifier 30 are shorted to ground.

Figure 6:
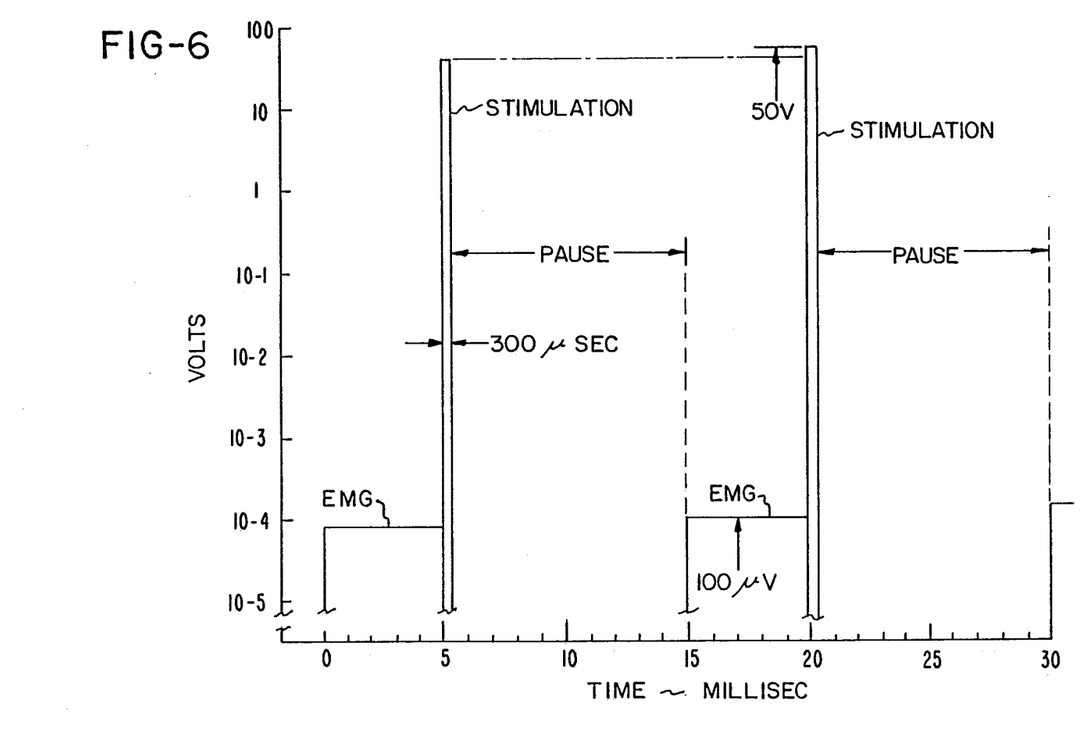
FIG. 6 is a timing diagram illustrating stimulation periods, pause periods and EMG sensing periods.

Integrated circuit 39 operated under control of synchronizing signals applied via line 22 to the base terminal of transistor 43. Output signals at the collector terminal of transistor 43 initiate operation of a timer in integrated circuit 39 which causes terminal No. 3 thereof to go HI for a period of about 10 milliseconds. This provides a corresponding pause period as illustrated in FIG. 6. The duration of the pause period is controlled by selection of the resistance of resistor 146 and the capacitance of capacitor 209. During that pause period amplifier 31 effectively ignores variations in the signal being sensed by electrodes 11, 12. However, after the signal on terminal 3 of integrated circuit 39 goes LO, transistor 44 again becomes non-conductive, and amplifier 31 again begins seeing amplified EMG signals. This continues for about 5 milliseconds as illustrated in FIG. 6, after which another stimulation pulse is generated.

When integrated circuit 39 activates transistor 44 it also activates reed relay 56 to close a switch 59 between lines 57 and 58. Referring back to FIG. 3, it will be seen that lines 57 and 58 are connected to electrodes 11 and 12. Thus the activation of reed relay 56 shorts out electrodes 11 and 12. However, this does not occur instantaneously, as reed relay 56 has an inherent mechanical delay of about 2 milliseconds. That provides sufficient time for generation of a stimulation pulse. Thereafter electrodes 11 and 12 are temporarily shorted out so as to become discharged.

During the above mentioned 5 millisecond sensing period A.C. signals which bypass transistor 44 are applied to an RMS converter circuit comprising amplifier 31, diodes 185 and 186, resistors 153 through 157 and capacitor 212. Amplifier 31 and diode 185 cooperate to function as a precision diode which rectifies the A.C. signal. The rectified signal charges capacitor 212 during the 5 millisecond EMG sensing period. Thereafter during the stimulation period and the pause period capacitor 212 discharges through resistor 157. Resistor 157 is adjustable for controlling the discharge time for capacitor 212, while resistor 156 is adjustable for controlling the charging time of capacitor 212.

The charge on capacitor 212 provides a voltage which is amplified by amplifiers 32 and 33 for application to control line 21. Variable resistor 160 provides for adjustment of the gain produced by the combination of amplifiers 32 and 33. As stated previously, signals on control line 21 are applied to stimulator 17. Thus capacitor 212 acts as a memory device for storing control signal samples so as to prevent loss of the control signal while transistor switch 44 is closed.

Figure 5:
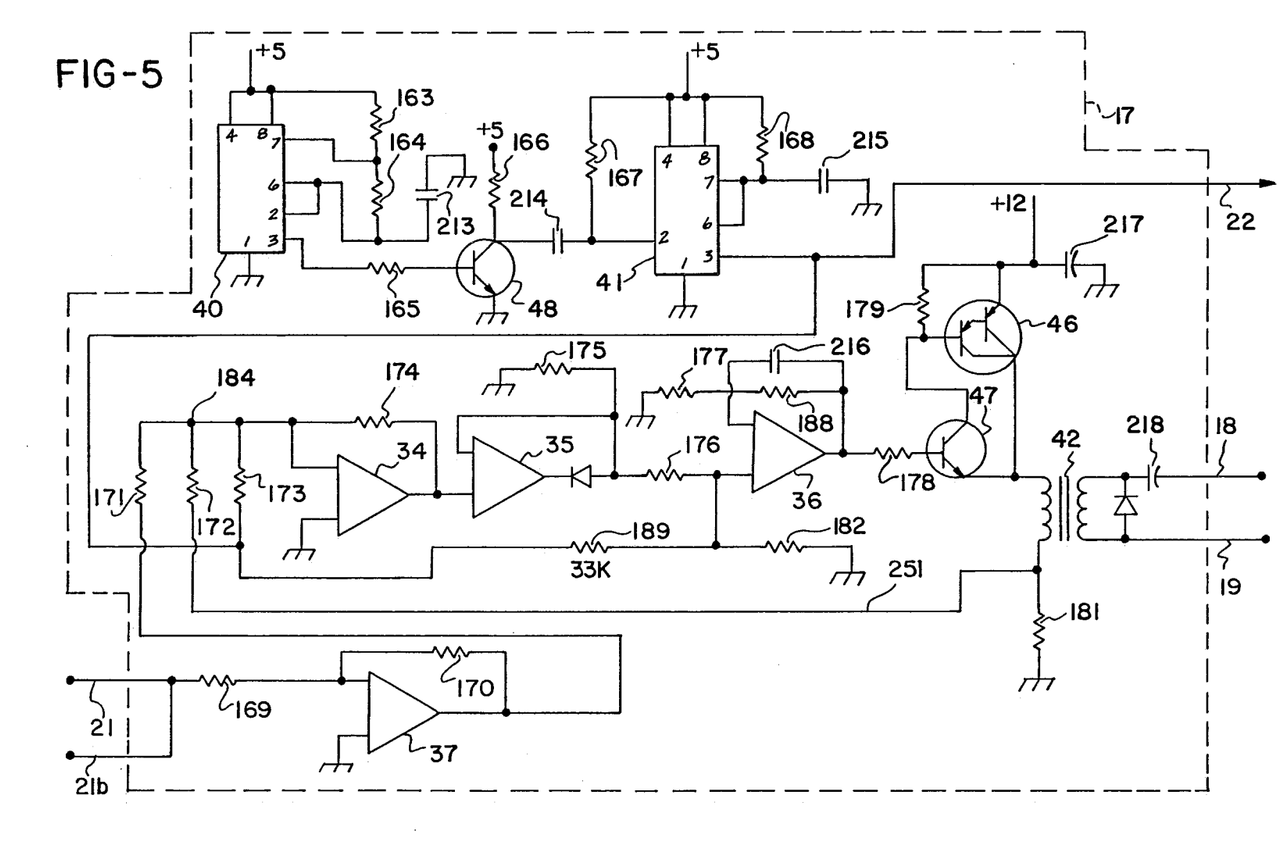
FIG. 5 is an electrical schematic diagram of a stimulation driving circuit.

The details of stimulator 17 are shown in FIG. 5. The output of this circuit is a series of pulses on lines 18, 19 having a current which is proportional to the voltage appearing on control line 21. The pulses persist for a duration of 300 microseconds and occur at a frequency of 65 Hz in synchronism with the above-mentioned synchronizing pulses occurring on line 22. Those synchronizing pulses are generated by integrated circuit 41 which operates under the control of transistor 48, integrated circuit 40 and a series of related resistors and capacitors connected as illustrated in FIG. 5. A similar arrangement of components for generation of stimulation timing pulses is disclosed in Petrofsky U.S. Pat. No. 4,558,704, and reference may be made to that patent for an operational description thereof.

The control signal supplied to stimulator 17 on control line 21 is amplified by amplifier 37 and applied to a summing junction 184 where it is compared with a feedback voltage on line 251. The voltage on line 251 is proportional to the current which flows to ground through resistor 181. As shown ,in FIG. 5, the current which passes through resistor 181 also passes through the primary side of an isolation transformer 42. A current of like magnitude flows through the secondary side of transformer 42, which in turn in connected via lines 18, 19 to electrodes 11, 12 for stimulation of the muscle therebelow.

The difference signal developed at summing junction 184 is amplified by amplifier 34 and applied to amplifier 35 which is connected for operation as a precision rectifier. A resistor 175 prevents the precision rectifier from drifting. The output from precision rectifier 35 is then integrated by an integrator comprising amplifier 36 and applied to a power amplifier comprising transistor 47 and Darlington amplifier 46. Darlington amplifier 46 provides the current for the primary side of isolation transformer 32. The network comprising amplifiers 34, 35 and 36, transistor 47 and Darlington 46 responds to a control voltage at summing junction 184 by generating an output current which produces a balancing voltage on feedback line 251. Thus the stimulation current and the stimulation effectivity are accurately controlled.

As also illustrated in FIG. 5, the synchronizing pulses generated at output terminal No. 3 of integrated circuit 41 are applied to the input terminals of amplifiers 34 and 36. This provides a bias which cuts off the stimulation current except when synchronizing pulses are being generated.

Figure 7:
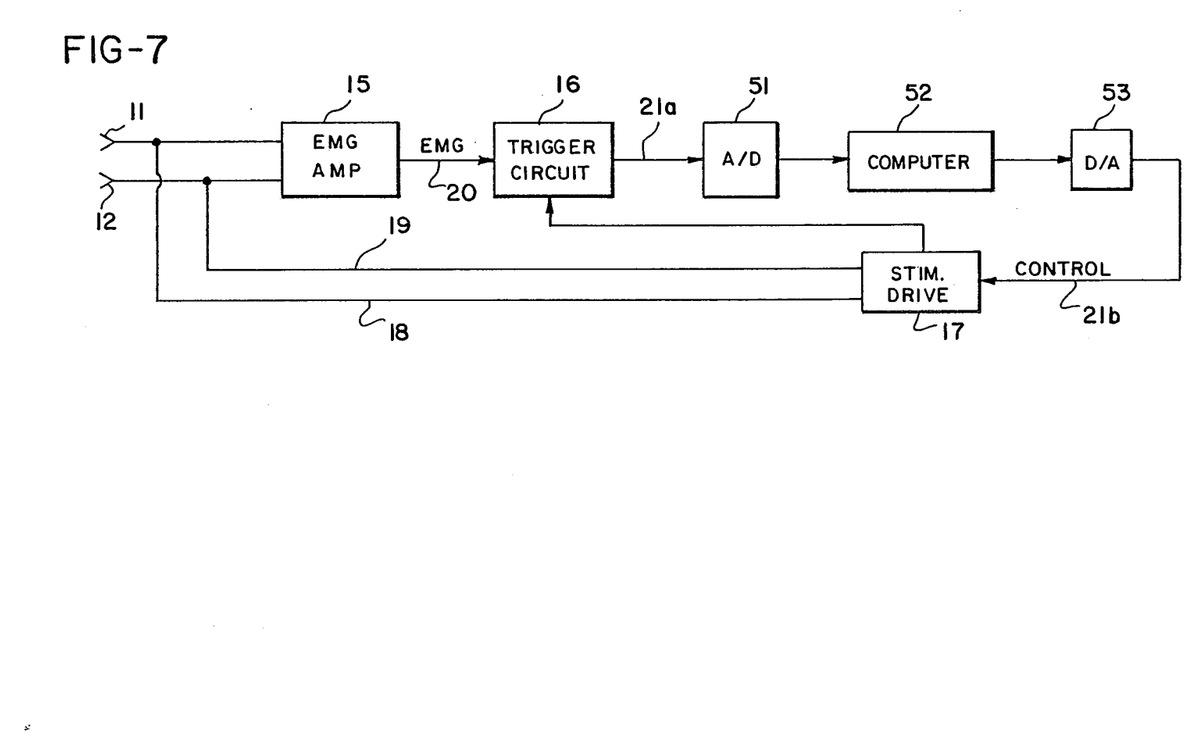
FIG. 7 is a generalized block diagram of the circuitry for an alternative embodiment of the invention.

In an alternative embodiment, the invention utilizes a miniaturized digital computer 52 connected as illustrated in generalized block diagram form in FIG. 7. In this embodiment the system utilizes only part of the circuitry of trigger circuit 16. In particular the system takes its output from trigger circuit 16 via line 21a of FIG. 4. This eliminates the RMS conversion and its associated downstream amplification.

For the alternative embodiment of FIG. 7, the rectified EMG signal on line 21a is applied to analog-to-digital converter 51 for digitizing. The digitized signal is supplied to computer 52 which may be programmed to provide a stimulation control signal which is linearly related to the EMG signal. However any other desired relationship may be programmed into computer 52, The output from computer 52 is applied to digital-to-analog converter 53 for conversion to analog format. The analog signal is then applied to stimulator 17 via line 21b. The computer memory stores samples of the control voltage appearing on line 21a, again preventing loss of the control signal while transistor switch 44 s closed.

Computer 52 may comprise a Z80 microprocessor programmed in accordance with techniques generally taught in Petrofsky U.S. Pat. No. 4,558,704. Reference may also be made to that patent for a teaching of appropriate electrical connections for computer 52 A/D converter 51 and D/A converter 53.

TABLE I

| Ref Numeral | Identification |
|---|---|
| 39 | LM555 (National Semiconductor) |
| 40 | LM555 (National Semiconductor) |
| 41 | LM555 (National Semiconductor) |
| 43 | 2N3904 |
| 44 | 2N3904 |
| 46 | D45E1 |
| 47 | 2N3904 |
| 48 | 2N3904 |
| 120 | 100K |
| 121 | 100K |
| 122 | 10K |
| 123 | 27K |
| 124 | 33K |
| 125 | 100K |
| 126 | 100K |
| 127 | 10K |
| 128 | 10K |
| 129 | 100K |
| 130 | 10K |
| 131 | 10K |
| 132 | 100K |
| 133 | 10K |
| 134 | 10K |
| 135 | 100K |
| 136 | 10K |
| 137 | 10K |
| 138 | 10K |
| 139 | 10K |
| 140 | 10K |

TABLE I-continued

| Ref Numeral | Identification |
| --- | --- |
| 141 | 22K |
| 142 | 100K |
| 143 | 500K |
| 144 | 1 M |
| 145 | 10 M |
| 146 | 18K |
| 147 | 5K |
| 148 | 1 M |
| 149 | 5K |
| 150 | 100 |
| 151 | 1K |
| 152 | 1K |
| 153 | 100 |
| 154 | 100 |
| 155 | 10K |
| 156 | 220K |
| 157 | 100K |
| 158 | 10K |
| 159 | 10K |
| 160 | 10K |
| 161 | 1K |
| 162 | 100K |
| 163 | 1K |
| 164 | 180K |
| 165 | 10K |
| 166 | 3.9K |
| 167 | 10K |
| 168 | 2.7K |
| 169 | 100K |
| 170 | 22K |
| 171 | 15K |
| 172 | 10K |
| 173 | 68K |
| 174 | 100K |
| 175 | 4.7K |
| 176 | 4.7K |
| 177 | 33K |
| 178 | 270 |
| 179 | 39K |
| 181 | 0.1 |
| 182 | 100K |
| 188 | 100K |
| 189 | 33K |
| 201 | 0.1 μf |
| 202 | 2200 μf |
| 203 | 0.1 μf |
| 204 | 2700 μf |
| 205 | 0.1 μf |
| 206 | 2700 μf |
| 207 | 2200 μf |
| 208 | .001 μf |
| 209 | 1 μf |
| 210 | 1 μf |
| 211 | 2700 μf |
| 212 | 10 μf |
| 213 | 0.1 μf |
| 214 | 0.008 μf |
| 215 | 0.1 μf |
| 216 | 0.001 μf |
| 217 | 10,000 μf |
| 218 | 1 μf |

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. Apparatus for assisting muscular contraction comprising:

electrode means for sensing voluntary electromyographic signals amplifier means connected to said electrode means for receiving and amplifying said electromyographic signals to produce a corresponding higher amplitude control signal, said control signal having a level varying in accordance with said electromyographic signals, signal limiting means connected between said amplifier means and said electrode means for limiting the level of signals applied by said electrode means to said amplifier means, stimulator means connected for receiving said control signal and comprising means responsive to said varying control signal level for generating and delivering to said electrode means a series of stimulation pulses each having an energy level which depends variably upon changes in the level of said control signal, and means for preventing said amplifier means from amplifying said stimulation pulses.

2. Apparatus according to claim 1 wherein said last named means comprises a transistor switch activated in synchronism with the generation of said stimulation pulses.

3. Apparatus according to claim 1, said electrode means comprising two electrode terminals and said signal limiting means comprising a pair of oppositely directed diodes interconnecting said terminals.

4. Apparatus according to claim 1 and further comprising memory means for storing samples of said control signal; said stimulator means being connected for generating said stimulation pulses in response to the values of said samples.

5. Apparatus according to claim 4 wherein said memory means comprises a capacitor.

6. Apparatus according to claim 4 wherein said memory means comprises a digital computer.

7. Apparatus for assisting muscular contraction comprising:

electrode means for sensing voluntary electromyographic signals, amplifier means connected to said electrode means for receiving and amplifying said electromyographic signals to produce corresponding higher amplitude control signals said control signal having a level varying in accordance with said electromyographic signals, signal limiting means associated with said amplifier means for preventing amplification of received signals which are in excess of a predetermined level, stimulator means connected for receiving said control signals and comprising means responsive to said varying control signal level for periodically delivering to said electrode means muscular stimulation signals which vary in dependence upon variations in said control signals, and switch means for disconnecting said stimulator means from said amplifier means while said stimulation signals are being delivered to said electrode means.

8. Apparatus according to claim 7 wherein said signal limiting means comprise diode means connected at the input side of said amplifier means for shunting past said amplifier means those received signals which are in excess of said predetermined level.

9. Apparatus according to claim 8 wherein said amplifier means comprise a plurality of series-connected amplifier stages and said signal limiting means comprise shunt-connected diode means at the input side of each of said amplifier stages.

10. Apparatus according to claim 7 wherein said switch means comprise means for disconnecting said stimulator from said amplifier means during a pause period which continues beyond the period of said stimulation signals and thereafter for a substantial proportion of the period of time between said stimulation signals.

11. Apparatus according to claim 10 wherein said switch means comprises timer means for causing said pause period to extend for a time approximately equal to two-thirds of the time between said stimulation signals.

12. Apparatus according to claim 11 wherein said stimulator means comprises means for generating a synchronizing signal in synchronism with said stimulation signals and said timer means comprises means connected to said stimulator means for reception of said synchronization signal, an integrated circuit responsive to said synchronization signal for generating a switching control signal and a transistor responsive to said switching control signal for causing said disconnection.

13. Apparatus according to claim 12 and further comprising means for shorting said electrode means together during at least a portion of said pause period.

* * * * *